(12) United States Patent
Murofushi et al.

(10) Patent No.: US 12,371,450 B2
(45) Date of Patent: Jul. 29, 2025

(54) CARBALYSOPHOSPHATIDIC ACID

(71) Applicant: Kimiko Murofushi, Tokyo (JP)

(72) Inventors: Kimiko Murofushi, Tokyo (JP); Mari Gotoh, Tokyo (JP); Keiko Fukasawa, Tokyo (JP); Junken Aoki, Miyagi (JP)

(73) Assignee: Kimiko Murofushi, Tokyo (JP)

( * ) Notice: Subject to any disclaimer, the term of this patent is extended or adjusted under 35 U.S.C. 154(b) by 738 days.

(21) Appl. No.: 17/778,298

(22) PCT Filed: Nov. 20, 2020

(86) PCT No.: PCT/JP2020/043362
§ 371 (c)(1),
(2) Date: Nov. 10, 2022

(87) PCT Pub. No.: WO2021/100847
PCT Pub. Date: May 27, 2021

(65) Prior Publication Data
US 2023/0108750 A1    Apr. 6, 2023

(30) Foreign Application Priority Data

Nov. 22, 2019  (JP) ................................. 2019-211367

(51) Int. Cl.
C07F 9/38  (2006.01)

(52) U.S. Cl.
CPC .................................. *C07F 9/3808* (2013.01)

(58) Field of Classification Search
None
See application file for complete search history.

(56) References Cited

U.S. PATENT DOCUMENTS

| | | | |
|---|---|---|---|
| 8,017,597 B2 | 9/2011 | Murofushi et al. | |
| 8,722,649 B2 * | 5/2014 | Prestwich | C07F 9/3808 558/179 |
| 9,085,593 B2 | 7/2015 | Murofushi et al. | |
| 10,413,559 B2 | 9/2019 | Murofushi et al. | |
| 2004/0214799 A1 | 10/2004 | Mukai et al. | |
| 2009/0326256 A1 | 12/2009 | Murofushi et al. | |

FOREIGN PATENT DOCUMENTS

| | | |
|---|---|---|
| JP | 2002-308778 A | 10/2002 |
| JP | 2002-308779 A | 10/2002 |
| JP | 2012-056853 A | 3/2012 |
| WO | 02/094286 A1 | 11/2002 |
| WO | 2008/081580 A1 | 7/2008 |
| WO | 2014/115885 A1 | 7/2014 |

OTHER PUBLICATIONS

ISR issued in International Patent Application No. PCT/JP2020/043362, Dec. 22, 2020, translation.
IPRP issued in International Patent Application No. PCT/JP2020/043362, May 22, 2022, translation.
Baker, D. et al., "Carba analogs of cyclic phosphatidic acid are selective inhibitors of autotaxin and cancer cell invasion and metastasis", Journal of Biological Chemistry, vol. 281, 2006, pp. 22786-22791.
Gotoh et al., "Insights of cyclic phosphatidic acid function", Journal of Japanese Biochemical Society, vol. 90, No. 6, 2018, pp. 757-765.
Murakami-Murofushi K. et al., "Inhibition of Eukaryotic DNA Polymerase α with a Novel Lysophosphatidic Acid (PHYLPA) Isolated from Myxoamoebae of Physarum polycephalum*", J. Biol. Chem., 1992, pp. 21512-21517.
Shimizu et al. "Quantitative determination of cyclic phosphatidic acid and its carba analog in mouse organs and plasma using LC-MS/MS", Journal of Chromatography B 1076 (2018) pp. 15-21.
K. Fukasawa et al., "2-Carba-lysophosphatidic acid is a novel beta-lysophosphatidic acid analogue with high potential for lysophosphatidic acid receptor activation and autotaxin inhibition" Scientific Reports, vol. 11, 17360 (11 pages) 2021.
Keiko Fukasawa et al., "Biosynthesis of β-lysophosphatidic acid from cyclic phosphatidic acid by autotaxin, and bioactivity of a novel β-lysophosphatidic acid analogue, 2-carba-lysophosphatidic acid" The Lysophospholipid and Related Mediators Conference: From Bench to Clinic, online, Jul. 2021.

* cited by examiner

*Primary Examiner* — Brian J Davis
(74) *Attorney, Agent, or Firm* — GREENBLUM & BERNSTEIN, P.L.C.

(57) ABSTRACT

It is an object of the present invention to identify a novel analog of carbacyclic phosphatidic acid that is a cyclic phosphatidic acid derivative, and to clarify the physiological activity thereof. According to the present invention, a compound represented by the following formula (1) is provided:

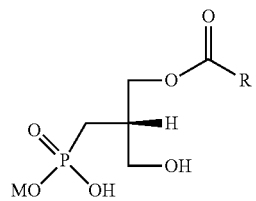

(1)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, and these groups may optionally comprise a cycloalkane ring or an aromatic ring; and M represents a hydrogen atom or a counter cation.

6 Claims, 13 Drawing Sheets

[Fig. 1]
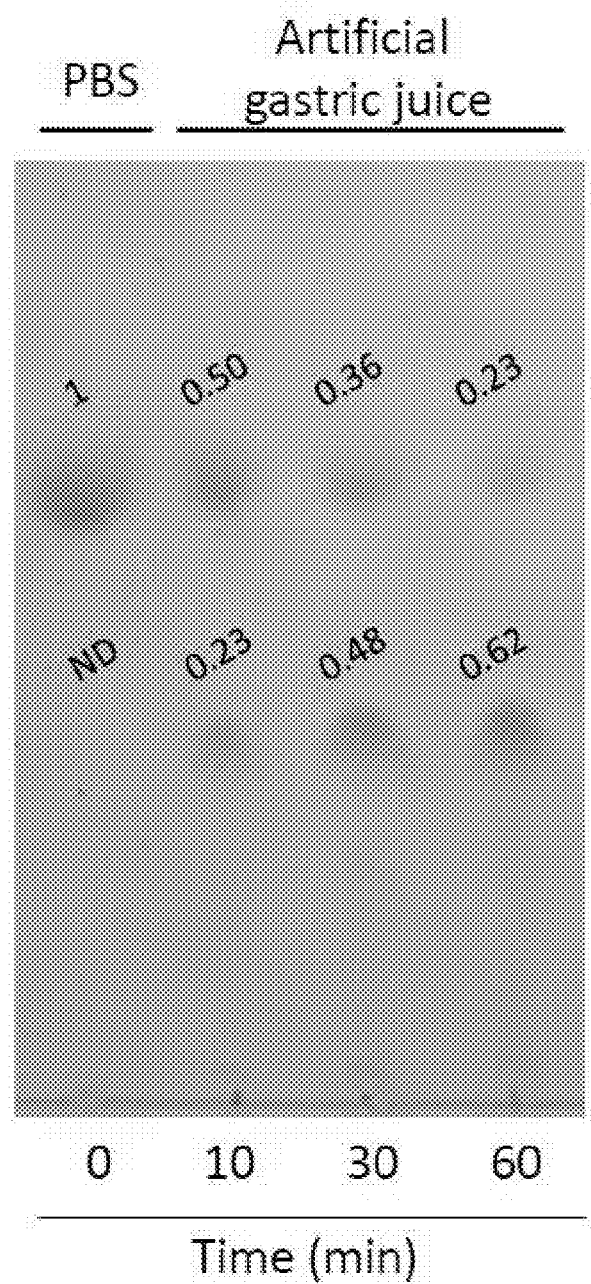

[Fig. 2]
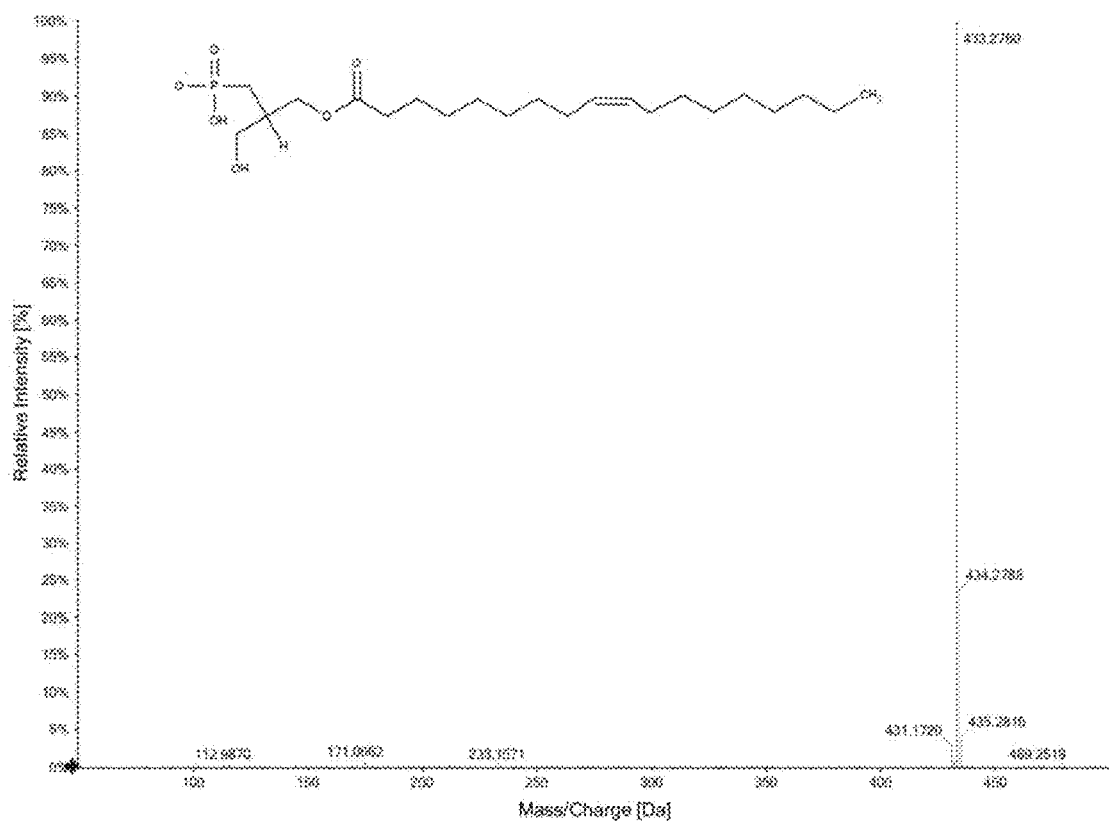

[Fig. 3]
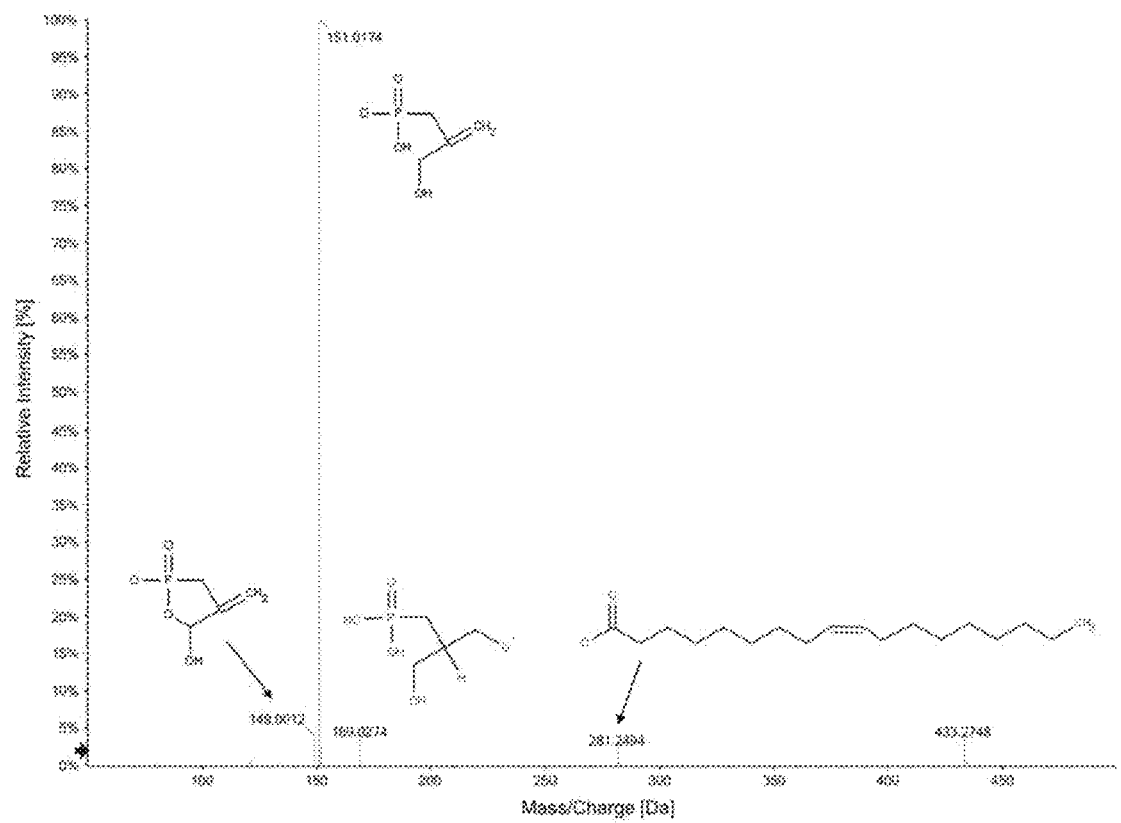

[Fig. 4]
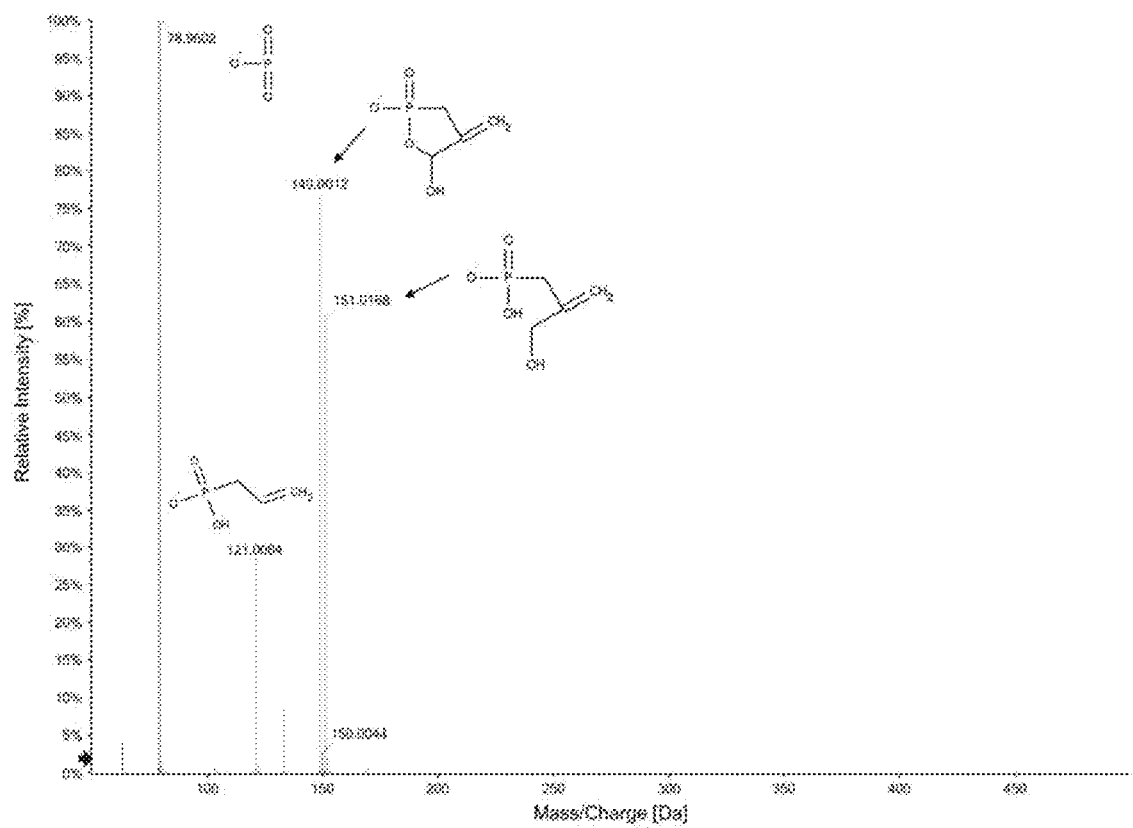

[Fig. 5]
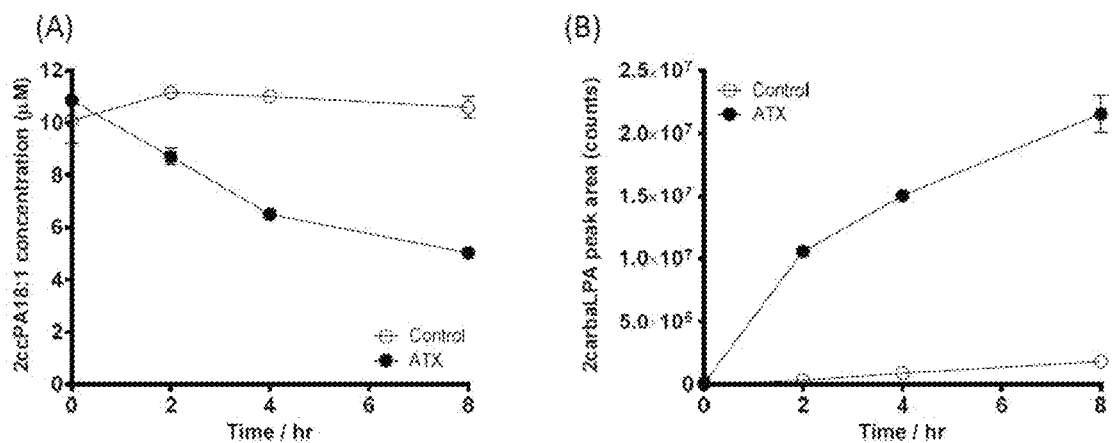
[Fig. 6]
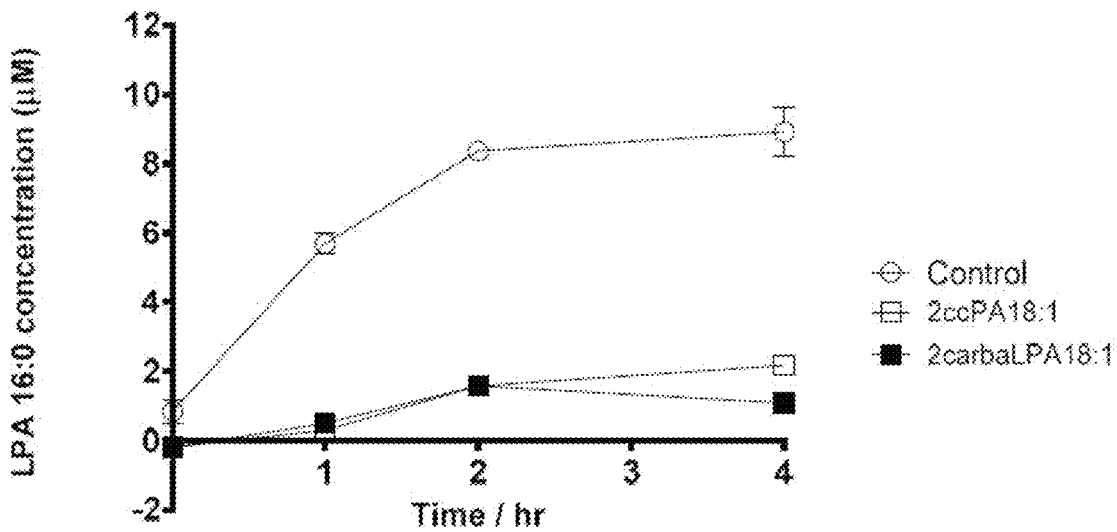

[Fig. 7]
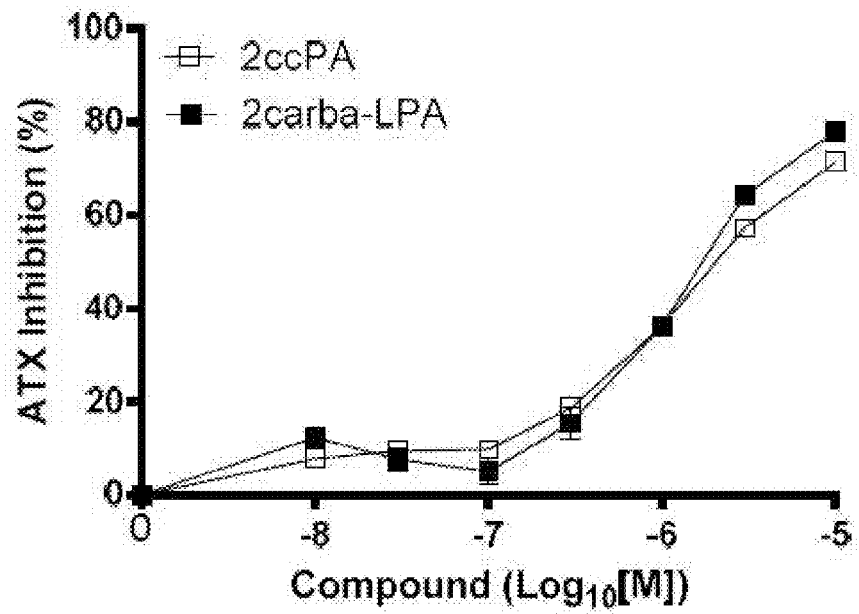
[Fig. 8]
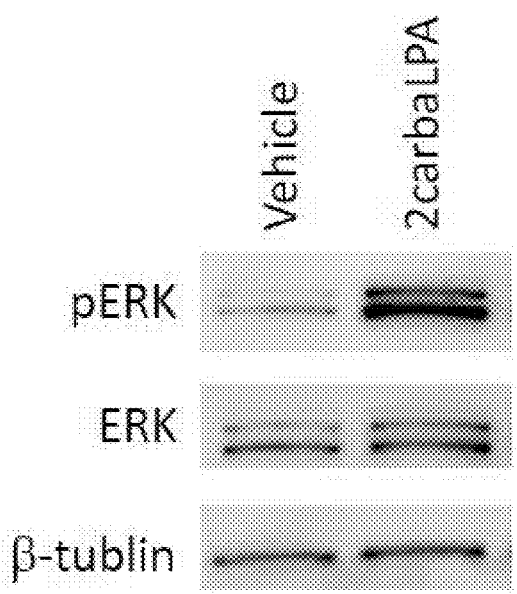

[Fig. 9]
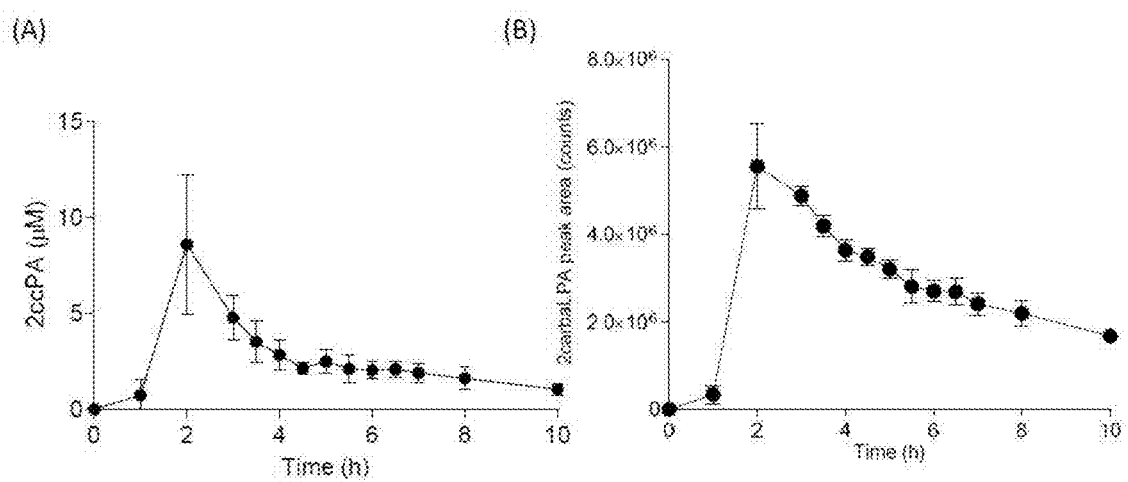

[Fig. 10]
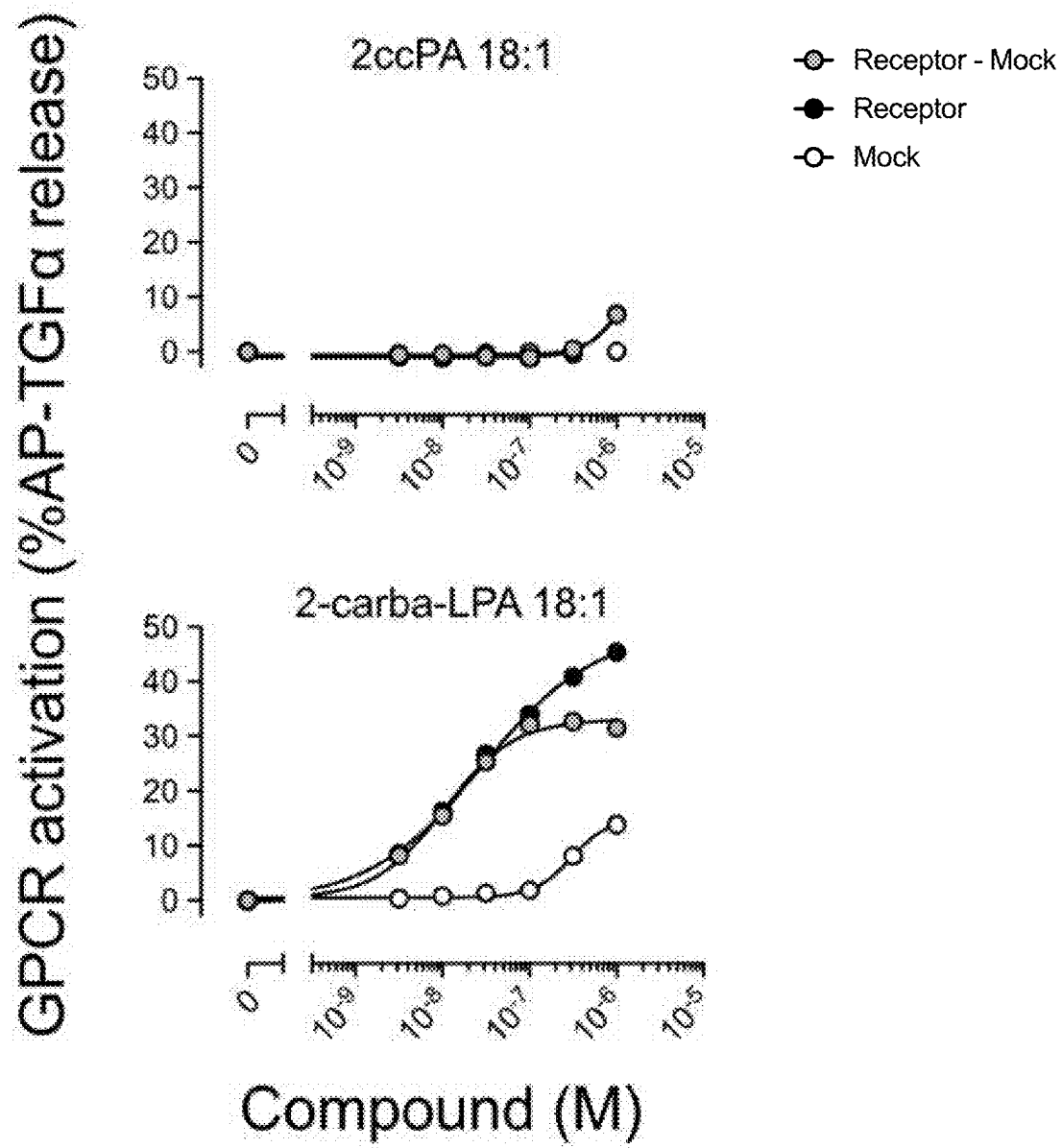

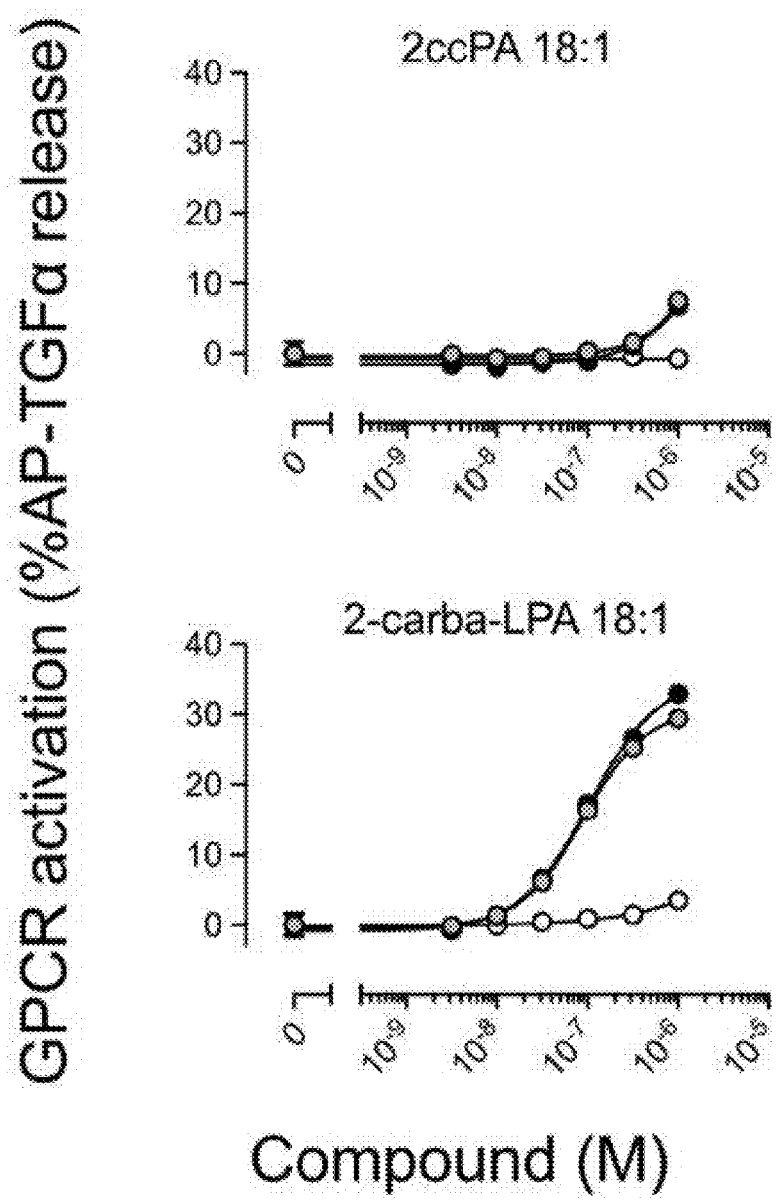
[Fig. 11]

[Fig. 12]
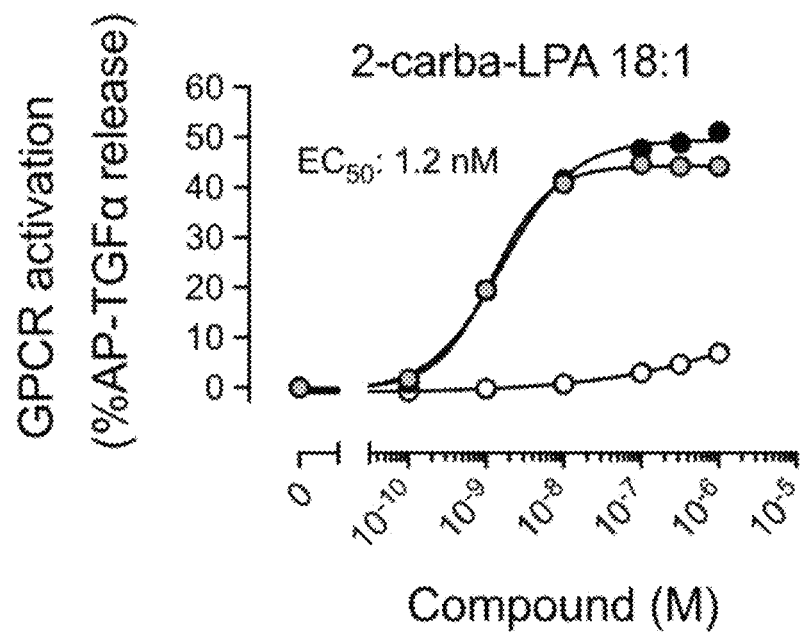

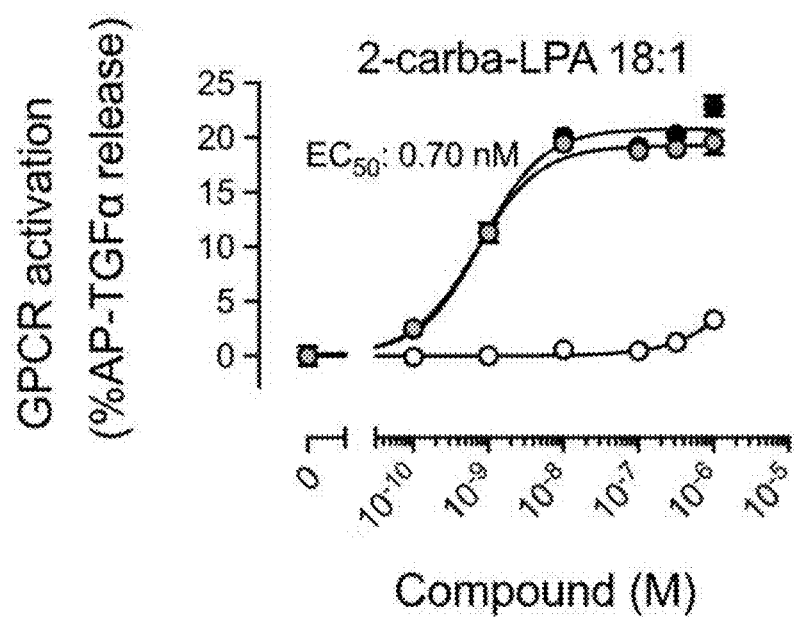
[Fig. 13]

[Fig. 14]
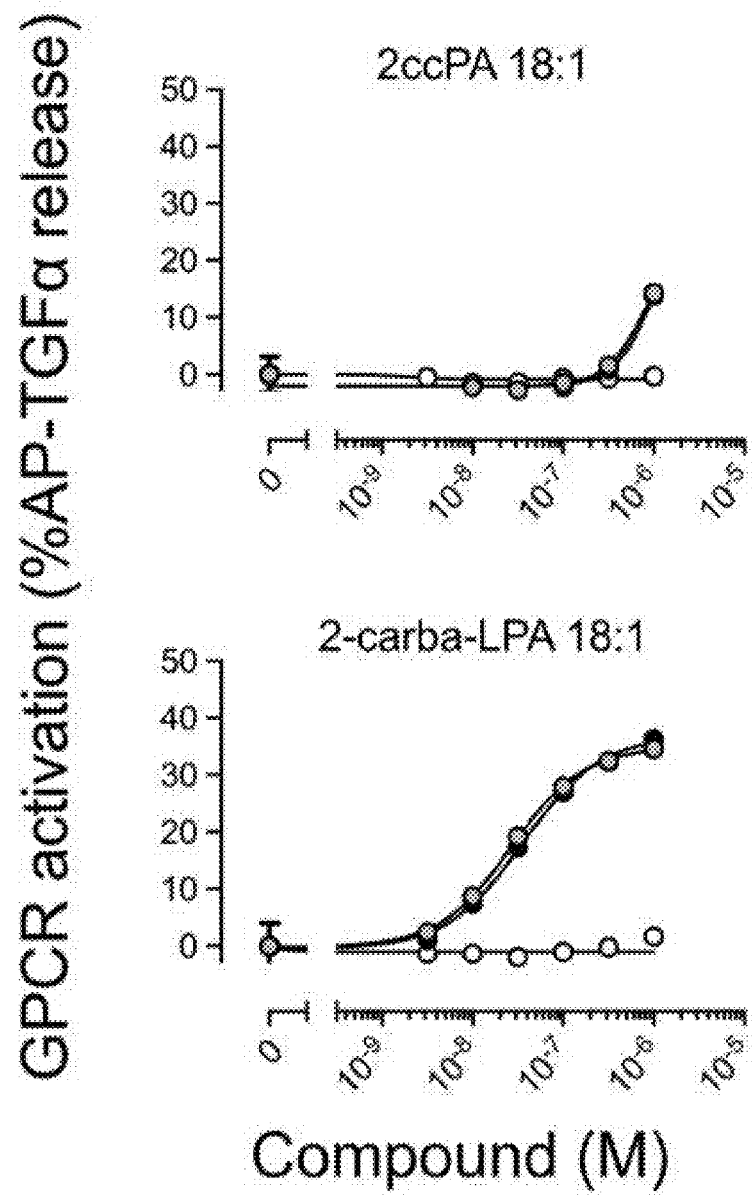

[Fig. 15]
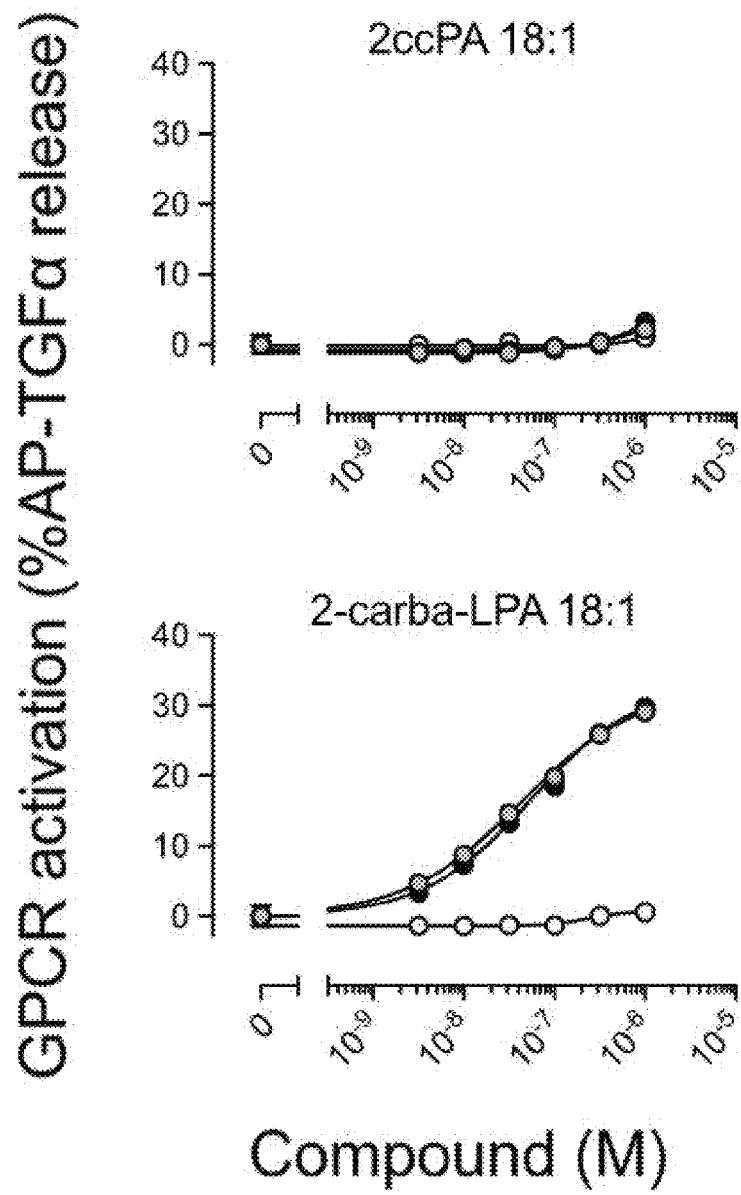

CARBALYSOPHOSPHATIDIC ACID

TECHNICAL FIELD

The present invention relates to carbalysophosphatidic acid having autotaxin inhibitory activity, LPA receptor-activating action, and ERK-phosphorylating action.

BACKGROUND ART

In 1992, a lipid-soluble substance that suppresses the activity of DNA polymerase a as a DNA synthesizing enzyme in eukaryotic cells and suppresses proliferation of cultured animal cells has been discovered from monophasic myxoamoeba of the acellular slime mold *Physarum polycephalum*, and this lipid-soluble substance has been isolated and purified (Non-Patent Document 1). This substance has been found to be a substance, in which hexadecanoic acid containing cyclopropane binds to position sn-1 of a glycerol backbone and phosphate group binds to positions 2 and 3 thereof via a cyclic ester bond. Since this substance is an LPA-like substance derived from *Physarum*, it was named as PHYLPA. PHYLPA has characteristic fatty acid at position sn-1. Thus, a derivative thereof was chemically synthesized by substituting the characteristic fatty acid with common fatty acid, and the activity thereof was then examined. As a result, it was demonstrated that PHYLPA suppresses cell proliferation, and it was revealed that the action of PHYLPA to suppress cell proliferation is caused by the cyclic phosphoric acid groups at position 2 and at position 3. At present, LPA analogs having such cyclic phosphoric acid groups are collectively referred to as "cyclic phosphatidic acid (cPA).

[Formula 1]

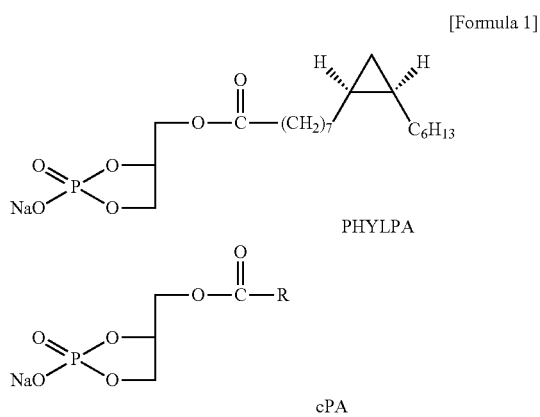

Regarding cyclic phosphatidic acid and a derivative thereof, there have been reports about neurotrophin action and application thereof to neurodegenerative disease (Patent Documents 1 and 2), suppression of proliferation of cancer cells and infiltration/metastasis thereof (Patent Document 3), analgesic action (Patent Document 4), application to atopic dermatitis (Patent Document 5), action to suppress demyelination of nerve axons (Patent Document 6), and the like.

PRIOR ART DOCUMENTS

Patent Documents

Patent Document 1: JP Patent Publication (Kokai) No. 2002-308778 A

Patent Document 2: JP Patent Publication (Kokai) No. 2002-308779 A

Patent Document 3: International publication WO 2002/94286

Patent Document 4: International publication WO 2008/81580

Patent Document 5: JP Patent Publication (Kokai) No. 2012-56853 A

Patent Document 6: International publication WO 2014/115885

Non-Patent Documents

Non-Patent Document 1: Murakami-Murofushi, K., et al., J. Biol. Chem. 267, 21512-21517 (1992)

SUMMARY OF INVENTION

Object to be Solved by the Invention

It is an object of the present invention to identify a novel analog of carbacyclic phosphatidic acid that is a cyclic phosphatidic acid derivative, and to clarify the physiological activity thereof.

Means for Solving the Object

The present inventors have discovered and identified carbalysophosphatidic acid as a novel analog of carbacyclic phosphatidic acid. The present inventors have further demonstrated that the above-described carbalysophosphatidic acid has autotaxin inhibitory activity, LPA receptor-activating action, and ERK-phosphorylating action. The present invention has been completed based on the above-described findings.

Specifically, according to the present invention, the following inventions are provided.

<1> A compound represented by the following formula (1):

[Formula 2]

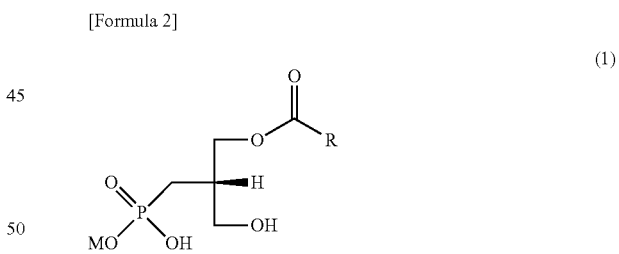

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, and these groups may optionally comprise a cycloalkane ring or an aromatic ring; and M represents a hydrogen atom or a counter cation.

<2> The compound according to the above <1>, wherein R represents a linear or branched alkyl group containing 9, 11, 13, 15 or 17 carbon atoms, or a linear or branched alkenyl group containing 9, 11, 13, 15 or 17 carbon atoms.

<3> The compound according to the above <1> or <2>, wherein —CO—R is a palmitoyl group or an oleoyl group.

<4> An autotaxin inhibitor comprising the compound according to any one of the above <1> to <3>.

<5> An LPA receptor activator comprising the compound according to any one of the above <1> to <3>.

<6> An ERK-phosphorylating agent comprising the compound according to any one of the above <1> to <3>.

According to the present invention, there is further provided a method for inhibiting autotaxin, comprising administering the compound represented by the formula (1) to a target (subject).

According to the present invention, there is further provided a method for activating an LPA receptor, comprising administering the compound represented by the formula (1) to a target (subject).

According to the present invention, there is further provided a method for phosphorylating ERK, comprising administering the compound represented by the formula (1) to a target (subject).

According to the present invention, there is further provided a compound represented by the formula (1) for use in inhibition of autotaxin.

According to the present invention, there is further provided a compound represented by the formula (1) for use in activation of an LPA receptor.

According to the present invention, there is further provided a compound represented by the formula (1) for use in phosphorylation of ERK.

According to the present invention, there is further provided use of the compound represented by the formula (1) for production of an autotaxin inhibitor.

According to the present invention, there is further provided use of the compound represented by the formula (1) for production of an LPA receptor activator.

According to the present invention, there is further provided use of the compound represented by the formula (1) for production of an ERK-phosphorylating agent.

Advantageous Effects of Invention

According to the present invention, novel carbalysophosphatidic acid is provided. The carbalysophosphatidic acid of the present invention has autotaxin inhibitory activity, LPA receptor-activating action, and ERK-phosphorylating action.

BRIEF DESCRIPTION OF DRAWINGS

FIG. 1 shows identification of a new spot of 2carbaLPA, using TLC.

FIG. 2 shows the results of the mass spectrometry of a compound.

FIG. 3 shows the results of the mass spectrometry of a compound.

FIG. 4 shows the results of the mass spectrometry of a compound.

FIG. 5 shows the results obtained by synthesizing 2carbaLPA using autotaxin (ATX).

FIG. 6 shows the results obtained by measuring the ATX activity inhibited by 2carbaLPA, using a mass spectrometer.

FIG. 7 shows the results obtained by measuring the activity of ATX to synthesize LPA using LPC as a substrate, which is inhibited by 2carbaLPA.

FIG. 8 shows the results obtained by measuring the ERK-phosphorylating action of 2carbaLPA.

FIG. 9 shows the results obtained by measuring 2carbaLPA generated in the body of a rat.

FIG. 10 shows the results obtained by measuring the agonist activity of 2ccPA and 2carbaLPA against human $LPA_1$.

FIG. 11 shows the results obtained by measuring the agonist activity of 2ccPA and 2carbaLPA against human $LPA_2$.

FIG. 12 shows the results obtained by measuring the agonist activity of 2carbaLPA against human $LPA_3$.

FIG. 13 shows the results obtained by measuring the agonist activity of 2carbaLPA against human $LPA_4$.

FIG. 14 shows the results obtained by measuring the agonist activity of 2ccPA and 2carbaLPA against human $LPA_5$.

FIG. 15 shows the results obtained by measuring the agonist activity of 2ccPA and 2carbaLPA against human $LPA_6$.

EMBODIMENT OF CARRYING OUT THE INVENTION

Hereinafter, the present invention will be more specifically described.

The present invention relates to a compound represented by the following formula (1):

[Formula 3]

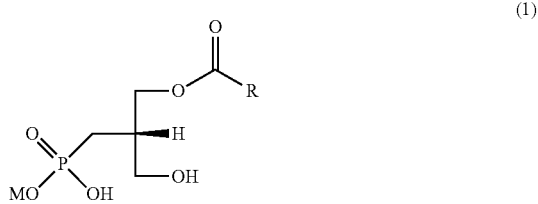

(1)

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, and these groups may optionally comprise a cycloalkane ring or an aromatic ring; and M represents a hydrogen atom or a counter cation.

Specific examples of the linear or branched alkyl group containing 1 to 30 carbon atoms represented by the substituent R in the formula (1) may include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

Specific examples of the linear or branched alkenyl group containing 2 to 30 carbon atoms represented by the substituent R may include an allyl group, a butenyl group, an octenyl group, a decenyl group, a dodecadienyl group, and a hexadecatrienyl group. More specific examples thereof may include an 8-decenyl group, an 8-undecenyl group, an 8-dodecenyl group, an 8-tridecenyl group, an 8-tetradecenyl group, an 8-pentadecenyl group, an 8-hexadecenyl group, an 8-heptadecenyl group, an 8-octadecenyl group, an 8-icosenyl group, an 8-docosenyl group, a heptadeca-8,11-dienyl group, a heptadeca-8,11,14-trienyl group, a nonadeca-4,7,10,13-tetraenyl group, a nonadeca-4,7,10,13,16-pentaenyl group, and a henicosa-3,6,9,12,15,18-hexaenyl group.

Specific examples of the linear or branched alkynyl group containing 2 to 30 carbon atoms represented by the substituent R may include an 8-decynyl group, an 8-undecynyl group, an 8-dodecynyl group, an 8-tridecynyl group, an 8-tetradecynyl group, an 8-pentadecynyl group, an 8-hexadecynyl group, an 8-heptadecynyl group, an 8-octadecynyl group, an 8-icosynyl group, an 8-docosynyl group, and a heptadeca-8,11-diynyl group.

Specific examples of the cycloalkane ring optionally contained in the above-described alkyl group, alkenyl group or alkynyl group may include a cyclopropane ring, a cyclobutane ring, a cyclopentane ring, a cyclohexane ring, and a cyclooctane ring. The cycloalkane ring may optionally contain one or more heteroatoms, and examples of such a cycloalkane ring may include an oxirane ring, an oxetane ring, a tetrahydrofuran ring, and an N-methylprolidine ring.

Specific examples of the aromatic ring optionally contained in the above-described alkyl group, alkenyl group or alkynyl group may include a benzene ring, a naphthalene ring, a pyridine ring, a furan ring, and a thiophene ring.

Accordingly, specific examples of the substituent R that is an alkyl group substituted with a cycloalkane ring may include a cyclopropylmethyl group, a cyclohexylethyl group, and an 8,9-methanopentadecyl group.

Specific examples of the substituent R that is an alkyl group substituted with an aromatic ring may include a benzyl group, a phenethyl group, and a p-pentylphenyloctyl group.

R is preferably a linear or branched alkyl group containing 9 to 17 carbon atoms, a linear or branched alkenyl group containing 9 to 17 carbon atoms, or a linear or branched alkynyl group containing 9 to 17 carbon atoms. R is more preferably a linear or branched alkyl group containing 9, 11, 13, 15 or 17 carbon atoms, or a linear or branched alkenyl group containing 9, 11, 13, 15 or 17 carbon atoms. R is particularly preferably a linear or branched alkenyl group containing 9, 11, 13, 15 or 17 carbon atoms.

Particularly preferably, in the above formula (1), —CO—R is a palmitoyl group or an oleoyl group.

M in the formula (1) is a hydrogen atom or a counter cation. Examples of M that is a counter cation may include an alkali metal atom, an alkaline-earth metal atom, and a substituted or unsubstituted ammonium group. Examples of the alkali metal atom may include lithium, sodium, and potassium. Examples of the alkaline-earth metal atom may include magnesium and calcium. Examples of the substituted ammonium group may include a butylammonium group, a triethylammonium group, and a tetramethylammonium group.

There may be a case where the compound represented by the formula (1) includes isomers such as positional isomers, geometric isomers, tautomers, or optical isomers, depending on the type of the substituent thereof. All possible isomers and mixtures comprising two or more types of the isomers at any given ratio are also included in the scope of the present invention.

The compound represented by the formula (1) may be present in the form of an adduct with water or various types of solvents (i.e. a hydrate or a solvate) in some cases. These adducts are also included in the scope of the present invention. In addition, any given crystal forms of the compound represented by the formula (1) and a salt thereof are also included in the scope of the present invention.

The compound represented by the formula (1) can be produced, for example, according to the method described in the after-mentioned Example 1 or Example 2.

Specifically, a solution is prepared by dissolving a carbacyclic phosphatidic acid derivative having the following structure in a suitable buffer (for example, a phosphate buffer, etc.):

[Formula 4]

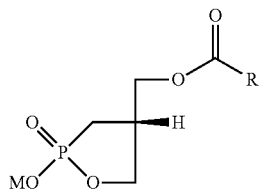

wherein R and M are the same as those defined in the formula (1). The thus prepared solution is diluted with an artificial gastric juice (for example, a sodium chloride aqueous solution (2 g of NaCl, 7 mL of 12 M HCl/1000 mL of water, pH 1.2)). The obtained solution is incubated, so that the compound represented by the formula (1) can be produced.

Alternatively, the compound represented by the formula (1) can be produced using autotaxin (ATX). ATX and a carbacyclic phosphatidic acid derivative having the above-described structure are dissolved in a suitable buffer (for example, a Tris buffer, etc.) to result in predetermined concentrations. The obtained solution is reacted by incubation at 37° C., so that the compound represented by the formula (1) can be produced.

The compound represented by the formula (1) of the present invention can be used as an autotaxin inhibitor, an LPA receptor activator, or an ERK-phosphorylating agent.

Autotaxin (ATX) is a phospholipid metabolizing enzyme, which decomposes lysophosphatidylcholine (LPC) and generates lysophosphatidic acid (LPA).

Lysophosphatidic acid (LPA) is one of lipid mediators associated with signal transduction, and binds to LPA receptors (6 types of G protein-coupled receptors).

ERK (Extracellular Signal-regulated Kinase) is a subfamily of MAPK that is activated by EGF, serum stimulation, oxidative stress, etc. Signals flow as a result of the binding of a ligand to a receptor such as an epidermal growth factor receptor (EGFR), and consequently, a TEY motif present in the activation loop of ERK is phosphorylated and activated.

The autotaxin inhibitor, LPA receptor activator or ERK-phosphorylating agent according to the present invention may be provided in the form of a reagent composition or a pharmaceutical composition, comprising the compound represented by the formula (1) as an active ingredient and one or two or more pharmaceutically acceptable preparation additives.

The autotaxin inhibitor, LPA receptor activator or ERK-phosphorylating agent of the present invention can be administered in various forms. A preferred administration form may be either oral administration or parenteral administration (e.g. intravenous, intramuscular, subcutaneous or intradermal injection, intrarectal administration, transmucosal administration, etc.). Examples of a pharmaceutical composition suitable for oral administration may include a tablet, a granule, a capsule, a powder agent, a solution agent, a suspension, and a syrup. Examples of a pharmaceutical composition suitable for parenteral administration may include an injection, drops, a suppository, and a transdermal absorbent. However, the dosage form of the autotaxin inhibitor, LPA receptor activator or ERK-phosphorylating agent of the present invention is not limited thereto. Furthermore, a prolonged action preparation can be produced using the compound of the present invention according to a known technique. For example, the compound of the present invention serving as an active ingredient is enclosed into hydrogel comprising gelatin as a base material, so as to produce a sustained release preparation.

The types of preparation additives, which are used in production of the autotaxin inhibitor, LPA receptor activator or ERK-phosphorylating agent of the present invention, are not particularly limited, and can be appropriately selected by a person skilled in the art. Examples of the preparation additives that can be used herein may include excipients, disintegrators or disintegration aids, binders, lubricants, coating agents, base materials, solubilizers or solubilizing agents, dispersants, suspending agents, emulsions, buffer agents, antioxidants, antiseptics, tonicity agents, pH adjusters, solubilizers, and stabilizers. Individual specific components used for these purposes are publicly known to such a skilled person.

Examples of the preparation additives that can be used in production of a preparation for use in oral administration may include: excipients, such as glucose, lactose, D-mannitol, starch, or crystalline cellulose; disintegrators or disintegration aids, such as carboxymethyl cellulose, starch, or calcium carboxymethyl cellulose; binders, such as hydroxypropyl cellulose, hydroxypropylmethyl cellulose, polyvinyl pyrrolidone, or gelatin; lubricants, such as magnesium stearate or talc; coating agents, such as hydroxypropylmethyl cellulose, white sugar, polyethylene glycol, or titanium oxide; and base materials, such as petrolatum, liquid paraffin, polyethylene glycol, gelatin, kaolin, glycerin, purified water, or hard fat.

Examples of the preparation additives that can be used in production of a preparation for use in injections or drops may include: solubilizers or solubilizing agents that may constitute aqueous injections or use-time dissolution type injections, such as distilled water, a normal saline, propylene glycol, and a surfactant, which are for use in injections; tonicity agents, such as glucose, sodium chloride, D-mannitol, and glycerin; and pH adjusters, such as inorganic acids, organic acids, inorganic bases, or organic bases.

The autotaxin inhibitor, LPA receptor activator or ERK-phosphorylating agent of the present invention can be administered to mammals such as humans.

The applied dose of the autotaxin inhibitor, LPA receptor activator or ERK-phosphorylating agent of the present invention should be increased or decreased, as appropriate, depending on conditions such as the age, sex and body weight of a patient, symptoms, and an administration route. In general, the daily dose of an active ingredient per adult is in the range of approximately 1 µg/kg to approximately 1,000 mg/kg, and is preferably in the range of approximately 10 µg/kg to approximately 100 mg/kg. The above-described dose of drug may be administered once or divided over several administrations (e.g. about 2 to 4 times) per day.

The present invention will be specifically described in the following examples. However, these examples are not intended to limit the scope of the present invention.

EXAMPLES

Example 1: Identification of 2carbaLPA (1) Discovery of New Spot, Using TLC

2ccPA having the following structure was used.

[Formula 5]

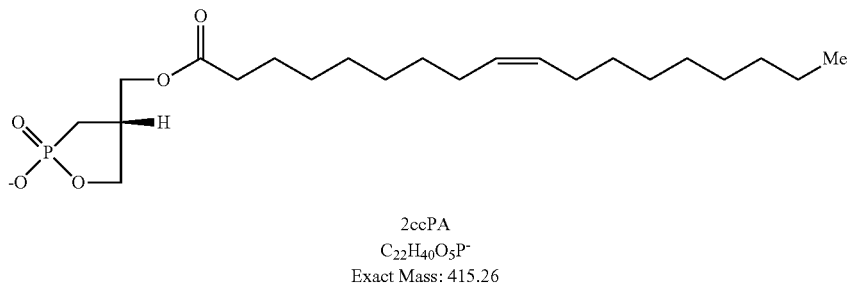

2ccPA
$C_{22}H_{40}O_5P^-$
Exact Mass: 415.26

2ccPA (5 mg) was dissolved in 1 mL of a phosphate buffer, and a 2ccPA/PBS solution was then diluted with the artificial gastric juice described in the Japanese Pharmacopoeia, 17th Edition (a sodium chloride aqueous solution (2 g of NaCl, 7 mL of 12 M HCl/1000 mL of water, pH 1.2) to result in a final concentration of 1 mg/mL. Thereafter, this solution was incubated at 37° C. for 10, 30, or 60 minutes. After completion of the reaction, the solution was developed onto a thin-layer chromatography plate (TLC silica gel 60 plate, (Merck)), using a developing solvent (chloroform/methanol/water=60:30:4 (v/v/v)). After completion of the separation, a copper acetate-phosphoric acid reagent (3% copper(II) acetate monohydrate (w/v), 8% phosphoric acid (v/v), and 2% sulfuric acid (v/v)) was sprayed onto the plate, and the plate was then heated at 150° C. for 5 minutes, so that the spots of the compound could be visualized (FIG. 1). The signal intensity of each spot was measured using ImageQuant LAS 4000 (GE healthcare UK Ltd., Buckinghamshire, UK), and was then quantified using ImageQuant TL, version 8.1 (GE healthcare) (the numerical values shown in FIG. 1). As a result, a new spot was confirmed to appear at a position, in which the Rf value (Rf value=about 0.29) was lower than that in the spot of 2ccPA (Rf value=about 0.35). In addition, it was shown that the signal intensity of this spot increased, as the incubation time passed.

Hence, in order to identify the compound at a new spot with Rf value=about 0.29, using the mass spectrometer Sciex Triple TOF4600 (QqTOF), the compound at the new spot was purified.

(2) Purification of New Spot

2ccPA (10 mg) was dissolved in 2 mL of the above-described artificial gastric juice (a sodium chloride aqueous solution (2 g of NaCl, 7 mL of 12 M HCl/1000 mL of water, pH 1.2). Thereafter, the temperature of this solution was set at 37° C., and 2 hours later, 8 mL of chloroform:methanol (2:1, v/v) was added to the solution. The solution was suspended, and was then separated into two layers according to centrifugation (1500 g×5 minutes). Thereafter, a lower layer was fractionated. The obtained chloroform-containing lower layer solution was developed onto a thin-layer chromatography plate, using a developing solvent (chloroform/methanol/water=60:30:4 (v/v/v)). Thereafter, silica gel at a portion on which a new spot was developed was scraped off, and was then suspended in 8 mL of a chloroform:methanol (1:9, v/v) solution. The suspension was subjected to an ultrasonic wave treatment in a water bath for 3 minutes, and was then centrifuged (1500 g×10 minutes), and thereafter, a supernatant was recovered. This operation was repeated three times. The recovered supernatant was dried with nitrogen, and was then dissolved in 1 mL of methanol, followed by filtration through a filter (0.2 µm Captiva Premium syringe filter, Agilent Technologies). The filtrate was dried with nitrogen, so as to obtain approximately 4.2 mg of a compound with an Rf value of about 0.29.

With regard to identification of the position of the new spot in the aforementioned thin-layer chromatography, the solution was developed onto a thin-layer chromatography plate, and a portion of the plate was then cut off. Thereafter, a copper acetate-phosphoric acid reagent (3% copper(II) acetate monohydrate (w/v), 8% phosphoric acid (v/v), and 2% sulfuric acid (v/v)) was sprayed onto the cut plate portion, and the plate portion was then heated at 150° C. for 5 minutes, so that the spot could be visualized and identified.

(3) Mass Spectrometry of Compound Using Sciex Triple TOF4600 (QqTOF)

The compound (approximately 4.2 mg) obtained in the above (2) was suspended in 10 mL of methanol, and the obtained solution was 100-fold diluted with 5 mM ammonium formate-containing methanol/water (95:5, v/v), so as to obtain a sample for Sciex Triple TOF4600 (QqTOF) mass spectrometer (measurement conditions will be shown in the following table). As a result of full ion scanning performed at 50-500 m/z, a molecular ion peak was obtained at 433.2760 (FIG. 2). Subsequently, this molecular ion was fragmented with collision energy (−30 or −75 eV), and the mass of the obtained fragment ions was then measured. As a result, at collision energy of −30 eV, fragment ions at 149.0012, 151.0174, 169.0274, and 281.2494 were obtained (FIG. 3), whereas at collision energy of −75 eV, fragment ions at 78.9602 and 121.0064 were also obtained (FIG. 4). Structural formulae assumed from individual molecular weights are shown in the figures (FIG. 2 to FIG. 4). These results demonstrated that the newly appearing spot is a compound with a molecular weight of 433.3 that can be formed by the hydrolysis of 2ccPA, and this compound was named as "2carbaLPA."

TABLE 1

| QqTOF conditions | |
|---|---|
| Items | Conditions |
| Ion source temperature | 0° C. |
| Curtain gas | 20 |
| Source gas 1 | 15 |
| Source gas 2 | 0 |
| Ion spray voltage | −4500 V |
| Declustering potential | −100 V |
| Scanning range (Cycle time, collision energy) | Full ion scan → m/z: 50-500 (250 ms, −10 eV) Product ion scan → m/z: 50-500 (100 ms, −30 or −75 eV) |

Example 2: Method of Synthesizing 2carbaLPA, Using Autotaxin (ATX)

ATX (Cayman chemical, MI) and 2ccPA were dissolved in 40 µL of a Tris buffer (50 mM Tris-HCl, pH 8.0, 140 mM NaCl, 5 mM KCl, 1 mM $CaCl_2$, and 1 mM $MgCl_2$), to result in final concentrations of 50 nM and 10 µM, respectively. Thereafter, the mixed solution was reacted at 37° C. for 0, 2, and 4 hours. After completion of the reaction, 160 µL of acetic methanol (pH 4.0) was added to and fully suspended in the reaction solution. Thereafter, the obtained solution was filtrated through a filter (0.2 µm Captiva Premium syringe filter, Agilent Technologies), so as to obtain a sample for QTRAP(registered trademark) 5500 triple quadrupole/linear ion trap mass spectrometer (SCIEX, Framingham, MA). The measurement was carried out in the same manner as that described in the study paper (Journal of Chromatography B 1076 (2018) 15-21, Quantitative determination of cyclic phosphatidic acid and its carba analog in mouse organs and plasma using LC-MS/MS). 2ccPA was measured at Q1/Q3=415.26/281.25, whereas 2carbaLPA was measured at Q1/Q3=433.27/151.02. As a result, it was demonstrated that the amount of 2ccPA was decreased in a time-dependent matter in the solution reacted with ATX (FIG. 5(A)), and that 2carbaLPA came to be synthesized (FIG. 5(B)).

Example 3: Inhibition of ATX Activity by 2carbaLPA (1) Measurement of ATX Activity Using Mass Spectrometer ATX and LPC 16:0 were suspended in 40 µL of a Tris buffer (50 mM Tris-HCl, pH 8.0, 140 mM NaCl, 5 mM KCl, 1 mM $CaCl_2$, and 1 mM $MgCl_2$) to result in final concentrations of 50 nM and 10 µM, respectively. Also, 2ccPA or 2carbaLPA was suspended in the aforementioned Tris buffer to result in a final concentration of 10 Thereafter, the obtained mixture was incubated at 37° C. At each reaction time, 160 µL of acidic methanol was added to and fully suspended in the reaction solution. Thereafter, the obtained solution was filtrated through a filter (0.2 µm Captiva Premium syringe filter, Agilent Technologies), so as to obtain a sample for QTRAP (registered trademark) 5500 triple quadrupole/linear ion trap mass spectrometer (SCIEX, Framingham, MA). The measurement was carried out in the same manner as that described in the study paper (Journal of Chromatography B 1076 (2018) 15-21, Quantitative determination of cyclic phosphatidic acid and its carba analog in mouse organs and plasma using LC-MS/MS). 2ccPA was measured at Q1/Q3=415.26/281.25, whereas 2carbaLPA was measured at Q1/Q3=433.27/151.02. Also, LPA was measured at Q1/Q3=409,24/153.00. The amount of LPA 16:0 that came to be synthesized at each reaction time was measured. As a result, it was demonstrated that LPA was synthesized in a time-dependent manner in the reaction solution containing neither 2ccPA nor 2carbaLPA, whereas the synthesis of LPA was suppressed in the reaction solution containing 2ccPA or 2carbaLPA (FIG. 6).

(2) Measurement of ATX Activity by Choline Oxidase, Using LPC as Substrate

ATX and LPC 16:0 were dissolved in 100 μL of a choline oxidase reaction solution (0.05% 4-aminoantipyrine, 0.05% TOOS (N-Ethyl-N-(2-hydroxy-3-sulfopropyl)-3-methylaniline, sodium salt, and dihydrate), 1 unit of peroxidase, 1 unit of choline oxidase, 50 mM Tris-HCl, pH 8.0, 140 mM NaCl, 5 mM KCl, 1 mM $CaCl_2$, and 1 mM $MgCl_2$) to result in final concentrations of 50 nM and 300 μM, respectively. Also, 2ccPA or 2carbaLPA was dissolved in the aforementioned choline oxidase reaction solution to a final concentration of 0.01 to 10 μM. The thus obtained solution was dispensed in a 96-well plate (100 μL/well). Thereafter, the plate was incubated at 37° C. for 120 minutes. After completion of the incubation, absorbance (555 nm) was measured using a plate reader (Biotek (Winooski, VT) Cytation 3 plate reader). Inhibitory activity was calculated according to the equation: inhibitory activity (%)=(1−increased absorbance 120 minutes after addition of inhibitor/increased absorbance 120 minutes after non-addition of inhibitor)×100. As a result, it was found that 2ccPA and 2carbaLPA inhibit ATX activity in a concentration-dependent manner (FIG. 7).

Example 4: ERK-Phosphorylating Action of 2carbaLPA

SW1353 cells were seeded at a density of $3×10^4$ cells/well on a 6-well plate. On the following day, the cell culture solution was exchanged with a serum-free culture solution, and the cells were cultured for 6 hours. Thereafter, 2carbaLPA dissolved in 0.1% BSA/PBS or 0.1% BSA/PBS (Vehicle) was added to the culture to a final concentration of 10 μM. The obtained mixture was incubated at 37° C. for 30 minutes, and the cells were then recovered using a sample buffer (0.125 M Tris-HCl, pH 6.8, 4% SDS, 20% glycerol, 0.01% BPB, and 10% 2-mercaptoethanol. Thereafter, the protein was separated by SDS-PAGE, and the protein in the SDS-PAGE gel was transcribed onto a PVDF membrane according to a Western-blotting method. The transcribed protein was detected using an anti-pERK antibody, an anti-ERK antibody and an anti-β-tubulin antibody as primary antibodies, and using an anti-rabbit IgG antibody as a secondary antibody. As a result, as shown in FIG. 8, the band of pERK became dense, and thus, it was demonstrated that 2carbaLPA can phosphorylate ERK.

Example 5: Production of 2carbaLPA in Rat Body

2ccPA (19.70±1.39 mg) was enclosed in a capsule (size 9, Torpac Inc., Fairfield, NJ)). In order to create an enteric-coated capsule, the capsule was coated with Eudragit S100/L100 (4/1, 11 mg/cm², pH 6.8) (Evonik Japan Co., Ltd., Tsukuba, Japan). The thus obtained capsule was orally administered to 7-week-old SD rats (body weight: 190 to 220 g), into each of which a cannula had been transvenously inserted in advance, using a capsule injector (Natsume Seisakusho, Tokyo, Japan). The cannula-inserted rats were purchased from Oriental Yeast Co., Ltd. Blood (300 μL each) was recovered from a carotid artery catheter over time. $EDTA-Na_2$ (1 mg/mL) was added to the recovered blood, and the thus obtained blood was then centrifuged (1000×g, 10 minutes, 4° C.) to obtain plasma. The plasma sample was immediately frozen with liquid nitrogen, and was then preserved at −80° C. until the measurement. A lipid fraction was extracted from the plasma sample in the same manner as that described in the study paper (Journal of Chromatography B 1076 (2018) 15-21, Quantitative determination of cyclic phosphatidic acid and its carba analog in mouse organs and plasma using LC-MS/MS). The measurement of 2ccPA and 2carbaLPA using a mass spectrometer was carried out in the same manner as the measurement of ATX activity using a mass spectrometer described in Example 3(1). As a result, it was demonstrated that 2ccPA was detected from the blood sample, having "2 hours after initiation of the measurement" as a peak (FIG. 9A), and that 2carbaLPA was also detected from the blood sample, having almost the same above period of time as a peak (FIG. 9B).

Example 6: Evaluation of Activity Against Human LPA Receptors

HEK293A or $\Delta LPA_{2/5/6}$ HEK293A was suspended in a Dulbecco-modified Eagle's medium (DMEM supplemented with 10% fetal calf serum, 100 U/mL penicillin, and 100 μg/mL streptomycin) to result in a concentration of $2×10^5$ cells/mL, and the thus obtained suspension was then seeded on a dish having a diameter of 100 mm (10 mL/dish). Thereafter, the cells were incubated at 37° C. in 5% $CO_2$ for 24 hours.

The below-mentioned plasmid solution (500 μL) was mixed with a polyethyleneimine (PEI, Polysciences) solution (500 μL), and the mixed solution was then incubated at room temperature for 20 minutes. Thereafter, the reaction mixture was added dropwise into the culture supernatant (1 mL/dish). Thereafter, the cells were incubated at 37° C. in 5% $CO_2$ for 24 hours.

TABLE 2

| Plasmid solution | |
| --- | --- |
| Opti-MEM (Thermo Fischer Scientific) | 500 μL |
| Alkaline phosphatase labeled TGFα (AP-TGFα) expression vector | 2.5 μg |
| GPCR expression vector | 1 μg |

TABLE 3

| PEI solution | |
| --- | --- |
| Opti-MEM | 480 μL |
| 1 μg/mL PEI | 20 μL |

Mock-transfected cells were transfected with an empty vector, instead of a GPCR expression vector. In addition, $LPA_1$- and $LPA_5$-expressing cells and control cells thereof were also transfected with a $G\alpha_{q/i1}$ expression vector (0.5 μg/dish). On the other hand, $LPA_2$- and $LPA_4$-expressing cells and control cells thereof were also transfected with a $G\alpha_{q/s}$ expression vector (0.5 μg/dish). HEK293A cells were used for the expression of $LPA_1$ and $LPA_4$. $\Delta LPA_{2/5/6}$ HEK293A cells were used for the expression of $LPA_2$, $LPA_3$, $LPA_5$, and $LPA_6$. For all LPA receptors, human genes were used.

HEK293A and $\Delta LPA_{2/5/6}$HEK293A cells were washed with PBS. The resulting cells were peeled with 0.05% Trypsin/0.53 mM EDTA (2 mL/dish), and were then neutralized with DMEM (3 mL/dish). The cells were centrifuged (190×g, 5 min), and were then re-suspended in a Hank's balanced salt solution (HBSS supplemented with 5 mM HEPES (pH 7.4)) (10 mL/dish), followed by incubation at room temperature for 15 minutes. After completion of the centrifugation (190×g, 5 min), the cells were re-suspended in HBSS, and were then seeded on a 96-well plate (cell plate) ($LPA_1$-, $LPA_2$-, and $LPA_3$-expressing cells, and the mock-transfected cells thereof: 90 μL/well; $LPA_5$-, and $LPA_6$-expressing cells and the mock-transfected cells thereof: 80 μL/well, 1-2×10⁴cells/well).

The cells were incubated at 37° C. in 5% $CO_2$ for 30 minutes, and an agonist (2ccPA or 2carbaLPA) was added thereto in a concentration 10 times higher than the final concentration (10 μL/well; the compound was diluted with HBSS supplemented with 0.01% bovine serum albumin). Besides, regarding the wells, to which $LPA_4$-, $LPA_5$-, and $LPA_6$-expressing cells and the mock-transfected cells thereof had been added, 100 μM Ki16425 was added 5 minutes before addition of the agonist (10 μL/well).

The cells were incubated at 37° C. in 5% $CO_2$ for 60 minutes, and the plate was then centrifuged (190×g, 2 min). Thereafter, the obtained supernatant was transferred into another 96-well plate (supernatant plate) (80 μL/well). 1M p-nitrophenyl phosphate (containing 120 mM Tris-HCl (pH 9.5), 40 mM NaCl, and 10 mM $MgCl_2$) was dispensed in individual wells of the supernatant plate and the cell plate (80 μL/well). Immediately after the dispensing and 1 hour after the dispensing, OD405 was measured.

Calculation Method

AP-TGFα release (%)=$\Delta OD405_{Sup}/(\Delta OD405_{Sup}+\Delta OD405 cell) \times 125$ GPCR activation (%)=AP-TGFα release under stimulated conditions−AP-TGFα release under non-stimulated conditions $EC_{50}$ and $E_{max}$ were calculated by fitting the data to a 4-parameter logistic curve, using Graphpad Prism 6 (Graphpad).

The measurement results of the experiment are shown in FIG. 10 to FIG. 15.

2carbaLPA exhibited agonist activity against all of the LPA receptors ($LPA_1$, $LPA_2$, $LPA_3$, $LPA_4$, $LPA_5$, and $LPA_6$).

The agonist activities ($EC_{50}$) of 2carbaLPA against $LPA_1$, $LPA_2$, $LPA_3$, $LPA_4$, $LPA_5$, and $LPA_6$ were 10 nM, 90 nM, 1.2 nM, 0.7 nM, 27 nM, and 43 nM, respectively.

The invention claimed is:

1. A compound represented by the following formula (1):

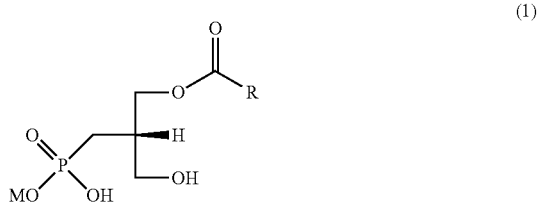

wherein R represents a linear or branched alkyl group containing 1 to 30 carbon atoms, a linear or branched alkenyl group containing 2 to 30 carbon atoms, or a linear or branched alkynyl group containing 2 to 30 carbon atoms, and these groups may optionally comprise a cycloalkane ring or an aromatic ring; and M represents a hydrogen atom or a counter cation.

2. The compound according to claim 1, wherein R represents a linear or branched alkyl group containing 9, 11, 13, 15 or 17 carbon atoms, or a linear or branched alkenyl group containing 9, 11, 13, 15 or 17 carbon atoms.

3. The compound according to claim 1, wherein —CO—R is a palmitoyl group or an oleoyl group.

4. An autotaxin inhibitor comprising the compound according to claim 1.

5. An LPA receptor activator comprising the compound according to claim 1.

6. An ERK-phosphorylating agent comprising the compound according to claim 1.

* * * * *